United States Patent
Zimmerman

(10) Patent No.: US 10,105,226 B2
(45) Date of Patent: Oct. 23, 2018

(54) OFFSET CARDIAC LEAFLET COAPTATION ELEMENT

(71) Applicant: Edwards Lifesciences Corporation, Irvine, CA (US)

(72) Inventor: Neil S. Zimmerman, Newport Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 199 days.

(21) Appl. No.: 15/019,706

(22) Filed: Feb. 9, 2016

(65) Prior Publication Data

US 2016/0228246 A1    Aug. 11, 2016

Related U.S. Application Data

(60) Provisional application No. 62/114,435, filed on Feb. 10, 2015.

(51) Int. Cl.
*A61F 2/24* (2006.01)

(52) U.S. Cl.
CPC ............ *A61F 2/2466* (2013.01); *A61F 2/246* (2013.01)

(58) Field of Classification Search
CPC ....... A61F 2/2466; A61F 2/246; A61F 2/2433
See application file for complete search history.

(56) References Cited

U.S. PATENT DOCUMENTS

| | | | |
|---|---|---|---|
| 5,735,842 A | 4/1998 | Krueger et al. | |
| 6,629,534 B1 | 10/2003 | St. Goar et al. | |
| 6,764,510 B2 | 7/2004 | Vidlund et al. | |
| 7,160,322 B2 | 1/2007 | Gabbay | |
| 7,404,824 B1 | 7/2008 | Webler et al. | |
| 7,556,646 B2 | 7/2009 | Yang et al. | |
| 7,678,145 B2 | 3/2010 | Vidlund et al. | |
| 7,785,366 B2 | 8/2010 | Maurer et al. | |
| 7,854,762 B2 | 12/2010 | Speziali et al. | |
| 7,942,928 B2 | 5/2011 | Webler et al. | |
| 8,080,808 B2 | 12/2011 | Norris | |
| 8,092,525 B2 | 1/2012 | Eliasen et al. | |
| 8,133,213 B2 | 3/2012 | Lashinski | |
| 8,449,606 B2 | 5/2013 | Eliasen et al. | |

(Continued)

OTHER PUBLICATIONS

Int'l. Search Report for PCT/US2016/017393, dated Jun. 3, 2016.

(Continued)

*Primary Examiner* — Richard Louis
(74) *Attorney, Agent, or Firm* — Guy Cumberbatch

(57) ABSTRACT

Systems, devices, and methods for reducing regurgitation through an atrioventricular heart valve: i.e., the mitral valve and the tricuspid valve. The device includes a flexible anchor rail anchored in the tissue of the ventricle and an offset coaptation element on a catheter that rides over the anchor rail and is positionable between the valve leaflets. The proximal end of the coaptation catheter is fixed subcutaneously adjacent the subclavian vein. The coaptation element includes an inert covering over a foam interior, and is radially offset on the catheter so that the foam body projects away from the septal side of the valve to reduce or minimize deformation from contact with the septal wall of the ventricle. Markers on the coaptation element facilitate positioning in the desired rotational orientation during delivery and implant.

18 Claims, 6 Drawing Sheets

(56) References Cited

U.S. PATENT DOCUMENTS

| | | | |
|---|---|---|---|
| 8,460,370 B2 | 6/2013 | Zakay | |
| 8,486,136 B2 | 7/2013 | Maurer et al. | |
| 8,579,967 B2 | 11/2013 | Webler et al. | |
| 8,758,432 B2 | 6/2014 | Solem | |
| 8,845,717 B2 | 9/2014 | Khairkhahan et al. | |
| 8,932,348 B2 | 1/2015 | Solem et al. | |
| 2003/0050694 A1 | 3/2003 | Yang et al. | |
| 2003/0187494 A1* | 10/2003 | Loaldi | A61F 2/856 623/1.11 |
| 2004/0098081 A1* | 5/2004 | Landreville | A61F 2/91 623/1.11 |
| 2004/0267280 A1* | 12/2004 | Nishide | A61F 2/958 606/108 |
| 2005/0038508 A1 | 2/2005 | Gabbay | |
| 2007/0038293 A1 | 2/2007 | St.Goar et al. | |
| 2007/0093890 A1 | 4/2007 | Eliasen et al. | |
| 2007/0162071 A1 | 7/2007 | Burkett et al. | |
| 2007/0185571 A1 | 8/2007 | Kapadia et al. | |
| 2007/0198082 A1 | 8/2007 | Kapadia et al. | |
| 2007/0219627 A1* | 9/2007 | Chu | A61B 17/0401 623/1.36 |
| 2007/0282429 A1 | 12/2007 | Hauser et al. | |
| 2008/0288061 A1 | 11/2008 | Maurer et al. | |
| 2009/0048668 A1 | 2/2009 | Wilson et al. | |
| 2009/0069885 A1 | 3/2009 | Rahdert et al. | |
| 2009/0069886 A1 | 3/2009 | Sun et al. | |
| 2009/0131880 A1 | 5/2009 | Speziali et al. | |
| 2009/0137968 A1 | 5/2009 | Rottenberg | |
| 2010/0198347 A1 | 8/2010 | Zakay et al. | |
| 2010/0298929 A1 | 11/2010 | Thornton et al. | |
| 2011/0077733 A1 | 3/2011 | Solem | |
| 2011/0224784 A1 | 9/2011 | Quinn | |
| 2011/0288577 A1 | 11/2011 | Newhauser et al. | |
| 2013/0325110 A1 | 12/2013 | Khalil et al. | |
| 2013/0338763 A1* | 12/2013 | Rowe | A61F 2/2427 623/2.11 |

OTHER PUBLICATIONS

Extended Search Report for EP13791015.4, dated Jan. 22, 2016.
Supplementary Search Report for EP13790562.6, dated Jan. 22, 2016.

* cited by examiner

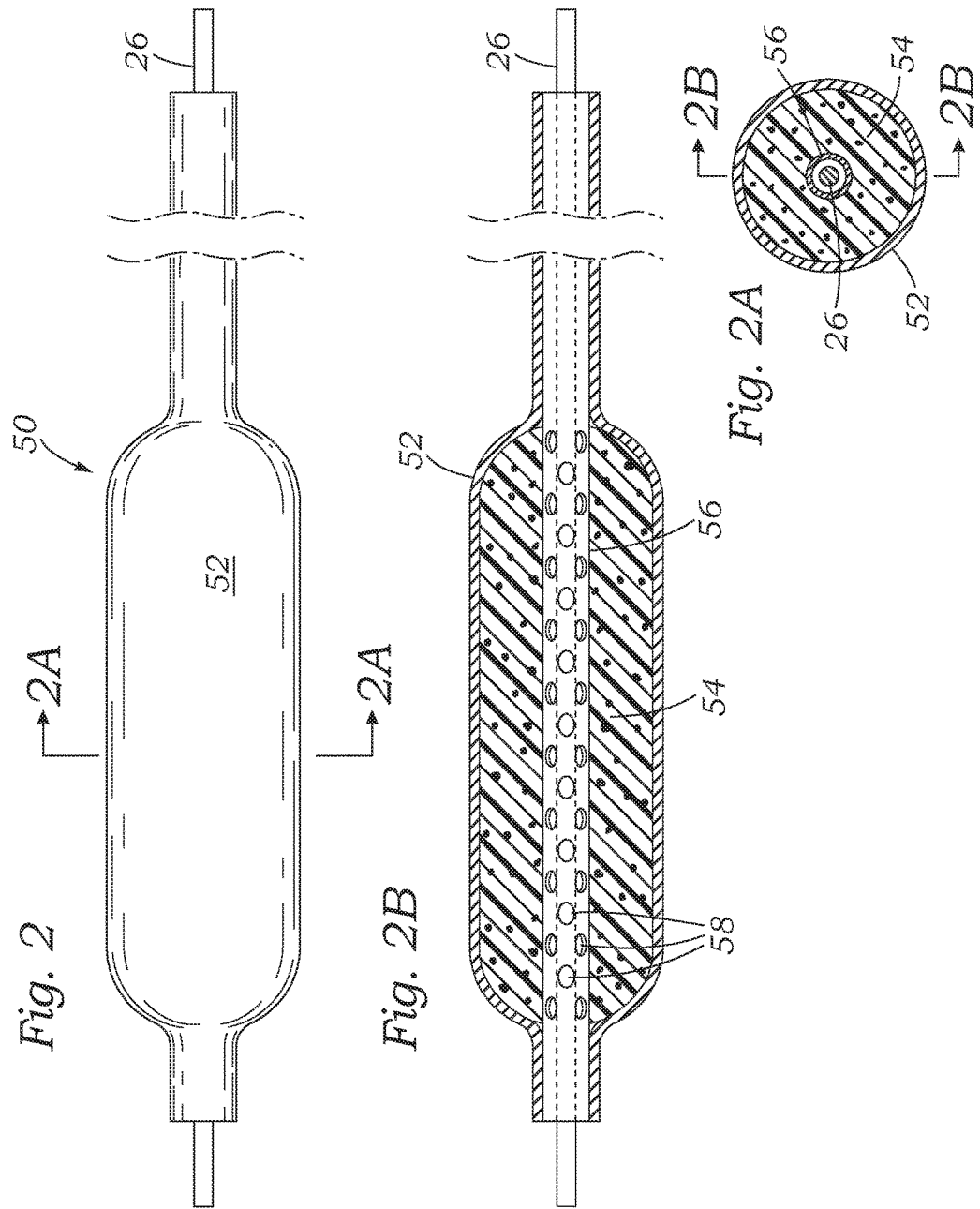

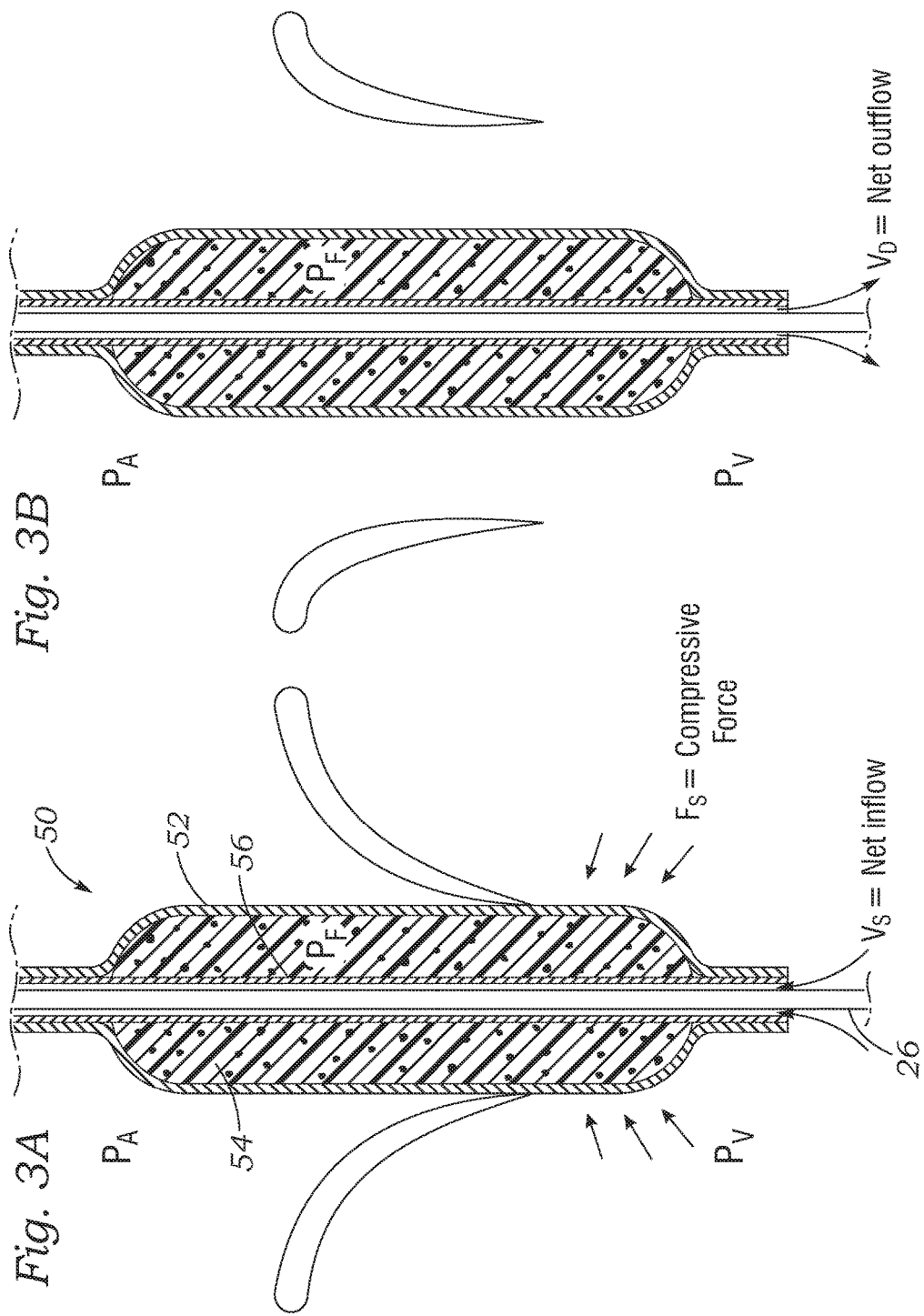

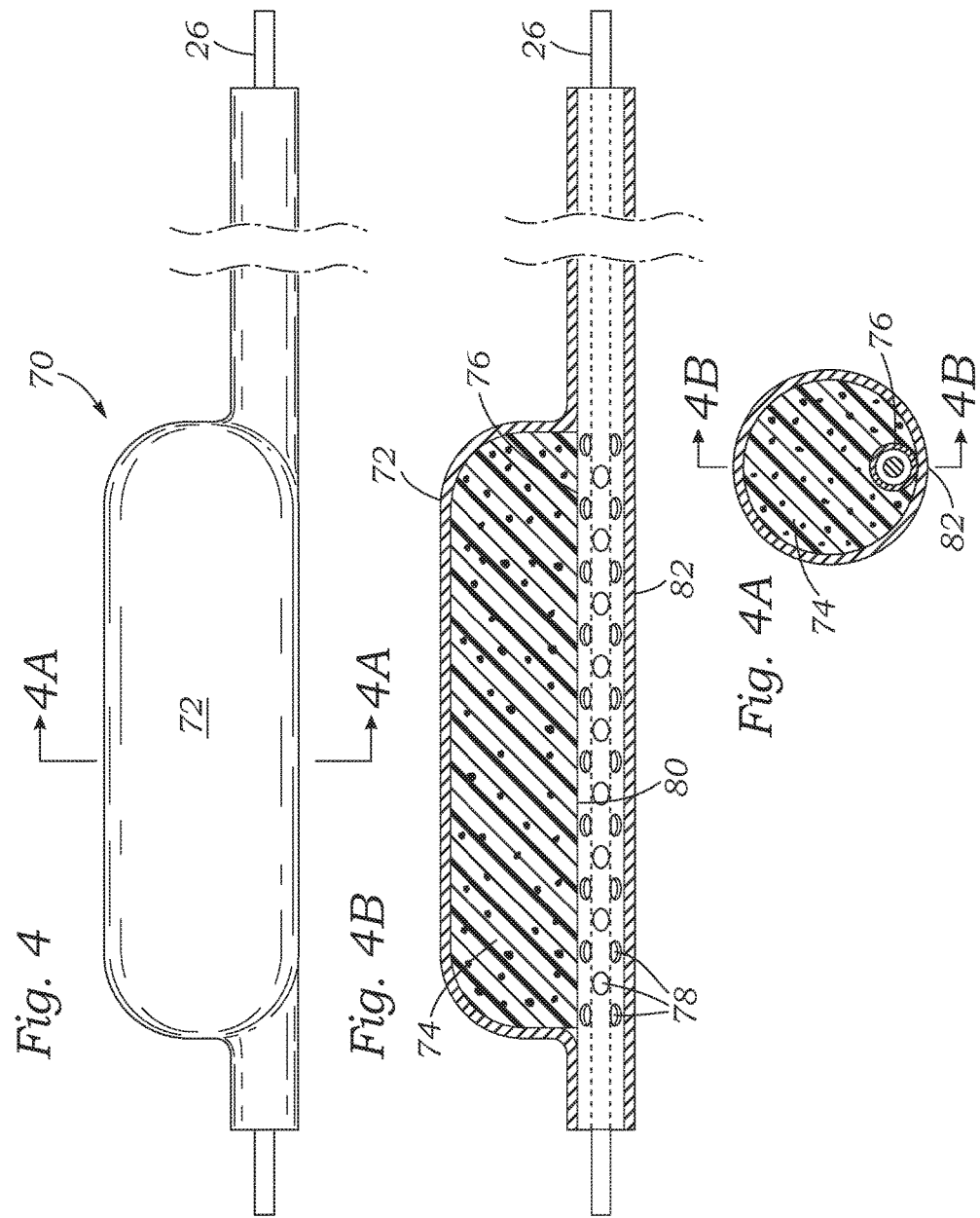

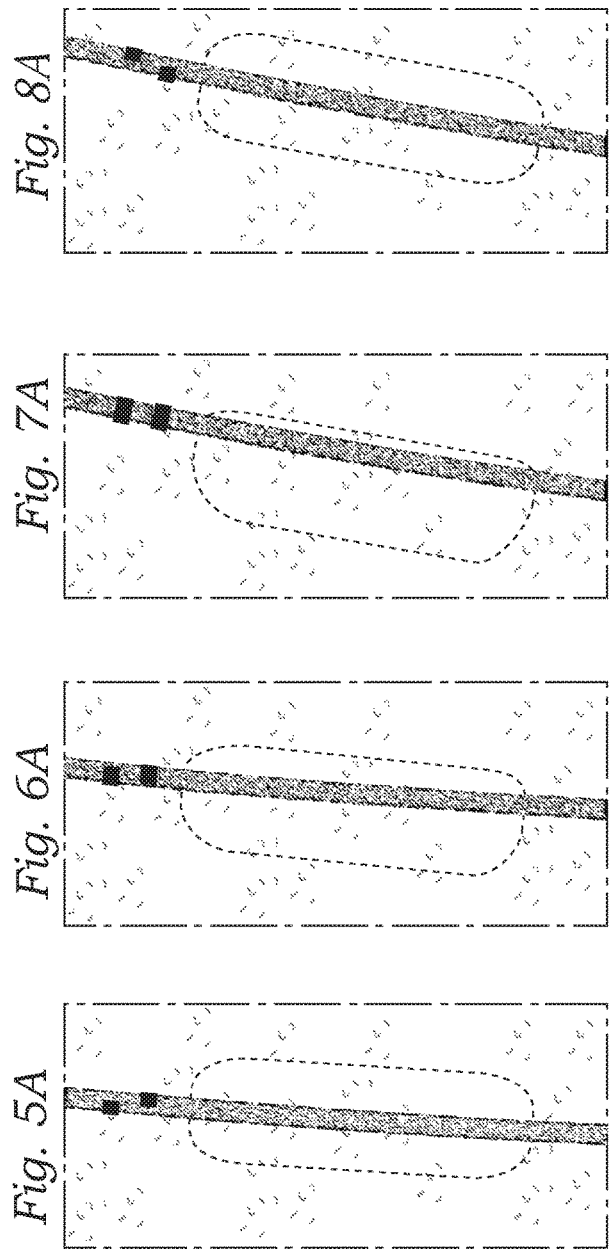
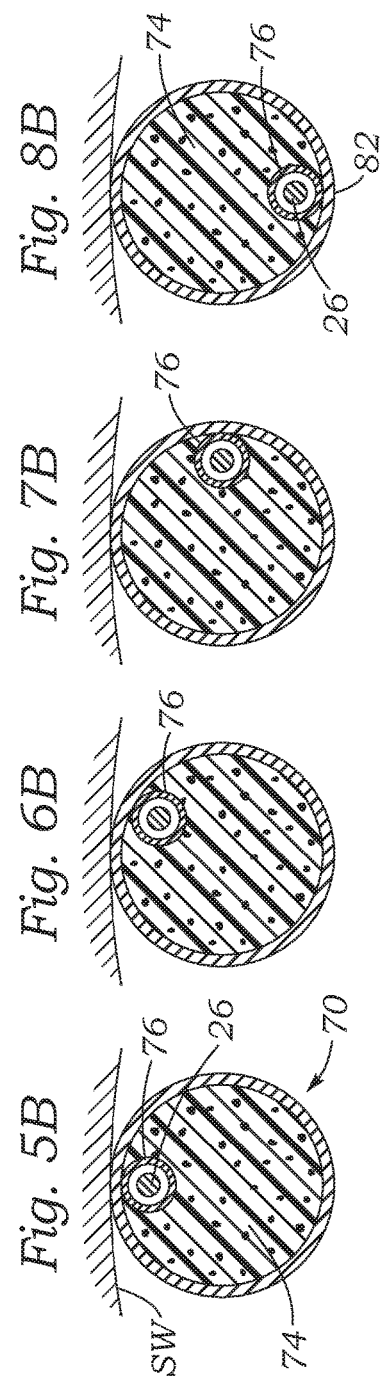

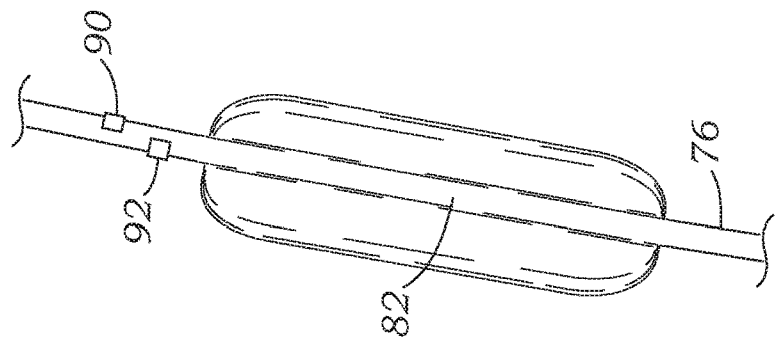
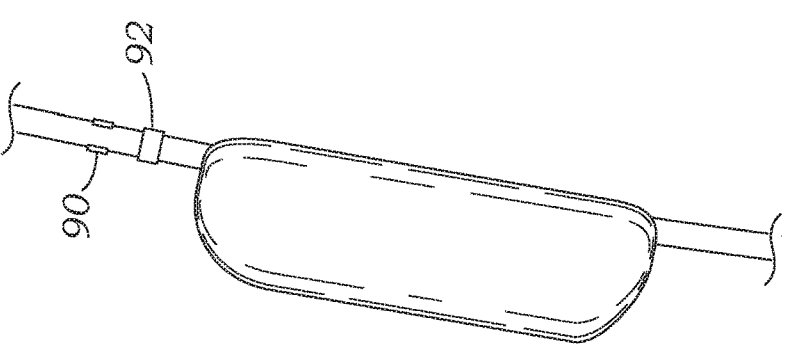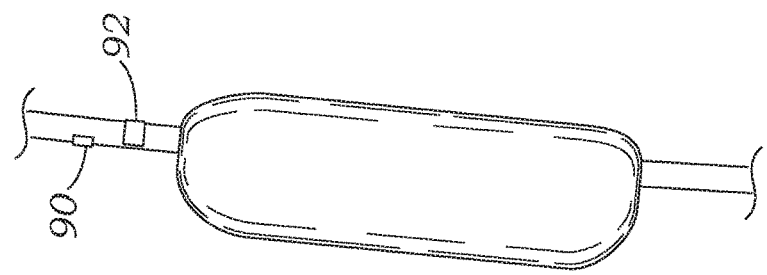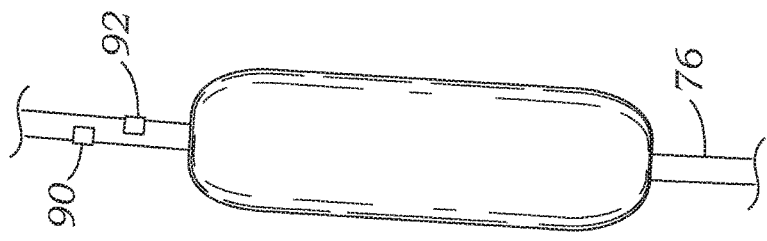

OFFSET CARDIAC LEAFLET COAPTATION ELEMENT

RELATED APPLICATIONS

The present application which claims priority to U.S. Provisional Application No. 62/114,435, filed Feb. 10, 2015, the entire disclosure of which is incorporated herein by reference.

TECHNICAL FIELD

The present invention relates generally to devices and methods for reducing regurgitation through an atrioventricular heart valve and, more particularly, to coaptation elements adapted to be positioned within the valve leaflets and maintain their proper shape.

BACKGROUND

The function of the heart may be seriously impaired if any of the heart valves are not functioning properly. The heart valves may lose their ability to close properly due to, e.g., dilation of an annulus around the valve, ventricular dilation, or a leaflet being flaccid causing a prolapsing leaflet. The leaflets may also have shrunken due to disease, e.g., rheumatic disease, thereby leaving a gap in the valve between the leaflets. The inability of the heart valve to close properly can cause a leak backwards (i.e., from the outflow to the inflow side), commonly referred to as regurgitation, through the valve. Heart valve regurgitation may seriously impair the function of the heart since more blood will have to be pumped through the regurgitating valve to maintain adequate circulation. Heart valve regurgitation decreases the efficiency of the heart, reduces blood circulation, and adds stress to the heart. In early stages, heart valve regurgitation leaves a person fatigued or short of breath. If left unchecked, the problem can lead to congestive heart failure, arrhythmia, or death.

Functional tricuspid regurgitation (TR), which accounts for the majority of all TR cases, occurs as a result of dilatation of the tricuspid annulus and enlargement of the right ventricle. These mechanisms are most often secondary to pulmonary hypertension, RV dysfunction, and left-sided valvular heart disease. Although early investigators hypothesized that TR would resolve upon correction of left-sided heart disease, subsequent studies have shown that severe TR often persists after left-sided valve interventions. Additionally, functional TR is increasingly recognized as a source of morbidity and a predictor for poor long-term survival.

Heart valve disease, such as valve regurgitation, is typically treated by replacing or repairing the diseased valve during open-heart surgery. Given that in functional TR the native valve leaflets exhibit no abnormal morphology, annular remodeling with a prosthetic ring has become the current gold standard for treatment; however, open-heart surgery is highly invasive and is therefore not an option for many patients. For functional TR patients too sick to undergo open-heart surgery due to other comorbidities or previous heart surgeries, a percutaneous treatment option is desirable. One such method is to position a structure between the valve leaflets so that the leaflets "coapt" against them, thereby helping to block regurgitant flow. However, to date designs for such "coaptation elements" fall short for one reason or another, including susceptibility to deformation over time that leads to a recurrence of regurgitation.

SUMMARY

The present disclosure relates generally to devices and methods for improving the function of a defective heart valve. The devices and methods disclosed herein are particularly well adapted for implantation in a patient's heart for reducing regurgitation through a heart valve. The devices and methods disclosed herein are particularly useful in reducing regurgitation through the two atrioventricular (AV) valves, which are between the atria and the ventricles—i.e., the mitral valve and the tricuspid valve.

In one embodiment, the device comprises: an anchor to deploy in the tissue of the right ventricle, a flexible anchor rail connected to the anchor, a coaptation element that rides over the anchor rail, a catheter attached to the proximal end of the coaptation element, a locking mechanism to fix the position of the coaptation element relative to the anchor rail, and a proximal anchoring feature to fix the proximal end of the coaptation catheter subcutaneously in the subclavian vein.

In a preferred aspect, a coaptation element comprises an offset balloon to minimize risk of foam compression and balloon wrinkling. The coaptation element is suitable for treating functional tricuspid regurgitation (TR) by occupying the regurgitant orifice of a dilated tricuspid valve, thus providing a new surface around which the native leaflets can coapt. An exemplary system comprises:

Anchor—engages the myocardium, securing the distal end of the device in the RV apex;

Railing shaft—connected to proximal end of anchor, serves as "railing" for the coaptation element;

Coaptation element—"gap filling" element that rides over the railing shaft, provides a coaptation surface for the native leaflets;

Coaptation shaft—reinforced polymer shaft, allows for delivery and adjustment of the coaptation element;

Locking mechanism—allows for subcutaneous fixation of the proximal end of the catheter.

One particularly preferred embodiment of the coaptation element further comprises the following components:

Polymer balloon—forms a smooth and atraumatic cylindrical surface for native leaflet coaptation;

Biocompatible foam—fills the balloon; expands upon delivery and provides structural support for the coaptation element;

Reinforced coaptation shaft—delivers the foam balloon over the railing shaft; reinforced structure resists long-term shaft compression; contains small holes under the foam to allow "passive inflation" of the balloon after delivery;

All three of these components, the polymer balloon, the biocompatible foam, and the coaptation shaft, are desirably manufactured from variants of polycarbonate urethane, a biocompatible polymer with a history of excellent stability in long-term implant scenarios.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures may be drawn to scale for some embodiments, the figures are not necessarily drawn to scale for all embodiments. Embodiments of the present disclosure will be described and explained with additional specificity and detail through the use of the accompanying drawings.

FIG. 2 is an assembled view and FIGS. 2A and 2B are sectional views of a coapting element with an outer cover surrounding an inner compressible member and with a perforated inner catheter for flow of fluid to and from the compressible member;

FIGS. 3A and 3B schematically illustrate the coapting element of FIG. 2 in section within a tricuspid valve during systole and diastole.

FIG. 4 is an assembled view and FIGS. 4A and 4B are sectional views of an offset coapting element with an outer cover surrounding an inner compressible member mounted on a delivery catheter such that the bulk of the coapting element is off center from the catheter;

FIGS. 5A-5B, 6A-6B, 7A-7B and 8A-8B are pairs of fluoroscopic images and sectional views of the offset coapting element in various orientations relative to an adjacent septal wall; and FIGS. 9A-9D are elevational views of the offset coapting element in the orientations of FIGS. 5-8 showing positioning of radiopaque orientation markers.

DETAILED DESCRIPTION OF CERTAIN EMBODIMENTS

Figure 1:
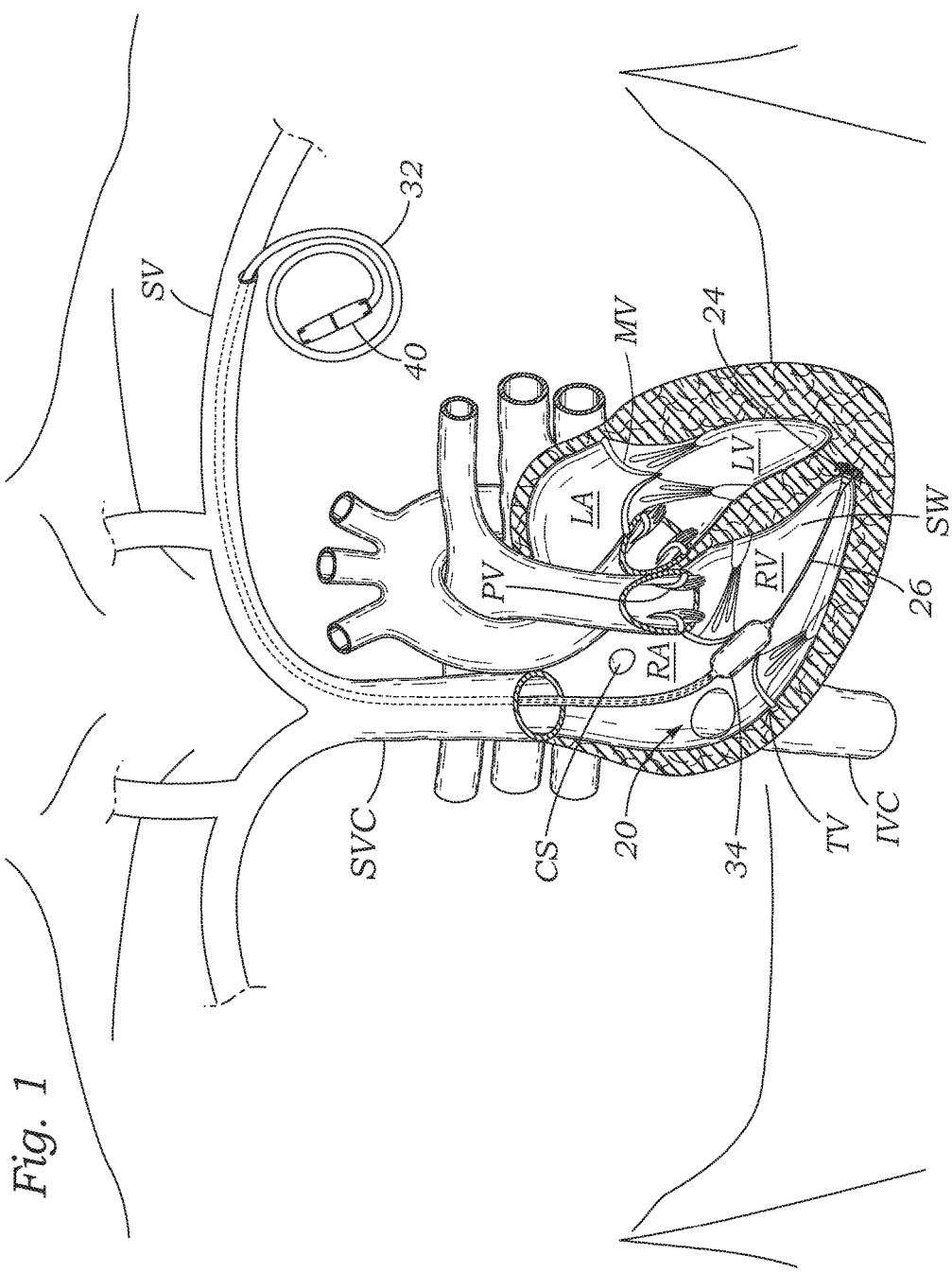
FIG. 1 is an overall view of the a regurgitation reduction device of the present application with a coapting element positioned between tricuspid valve leaflets and a proximal length of the delivery catheter including the locking collet shown exiting the subclavian vein to remain implanted subcutaneously.

Exemplary embodiments of the present disclosure are directed to devices and methods for improving the function of a defective heart valve. The following description refers to the accompanying drawings, which illustrate specific embodiments. Other embodiments having different structures and operation do not depart from the scope of the disclosure.

With reference to FIG. 1, the right ventricle RV and left ventricle LV of the heart are separated from the right atrium RA and left atrium LA, respectively, by the tricuspid valve TV and mitral valve MV—i.e., the atrioventricular valves. Each of these valves has flexible leaflets extending inward across the respective orifices that come together or "coapt" in the flowstream to form one-way, fluid occluding surfaces. The regurgitation reduction devices of the present application are primarily intended for use to treat the atrioventricular valves, and in particular the tricuspid valve.

An overall regurgitation reduction system 20 is seen extending from the apex of the right ventricle RV upward through the tricuspid valve TV, right atrium RA, superior vena cava SVC and into the subclavian vein SV with the heart shown in its systolic phase. Anatomical structures of the right atrium RA and right ventricle RV will be explained in greater detail, though it should be understood that the devices described herein may equally be used to treat the mitral valve MV.

The right atrium RA receives deoxygenated blood from the venous system through the superior vena cava SVC and the inferior vena cava IVC, the former entering the right atrium above, and the latter from below. The coronary sinus CS is a collection of veins joined together to form a large vessel that collects deoxygenated blood from the heart muscle (myocardium), and delivers it to the right atrium RA. During the diastolic phase, or diastole, the venous blood that collects in the right atrium RA is pulled through the tricuspid valve TV and into the right ventricle RV by expansion of the right ventricle. In the systolic phase, or systole, seen in FIG. 1, the right ventricle RV collapses and the tricuspid valve TV closes to force the venous blood through the pulmonary valve PV and pulmonary artery into the lungs. The leaflets of the tricuspid valve TV close to prevent the venous blood from regurgitating back into the right atrium RA. It is during systole that regurgitation through the tricuspid valve TV becomes an issue, and the devices of the present application are beneficial.

The regurgitation reduction system 20 includes a device anchor 24 attached to an elongated anchor rail 26, which in some versions is constructed to have good capacity for torque. For instance, the anchor rail 26 may be constructed as a braided wire rod or cable. A delivery catheter 32 slides concentrically over the anchor rail 26 and features a coapting element 34 on a distal end thereof adapted to be positioned within the tricuspid valve TV. The delivery catheter 32 extends upward through the right atrium RA and into the superior vena cava SVC and subclavian vein SV. A locking collet 40 on the proximal end of the catheter 32 exits the subclavian vein SV through a puncture and remains implanted subcutaneously; preferably coiling upon itself as shown.

An embodiment of a method for deploying the regurgitation reduction system 20 follows. In a first step to deploy the regurgitation reduction system 20, an anchoring catheter (not shown) enters the right atrium RA from the superior vena cava SVC after having been introduced to the subclavian vein (see FIG. 1) using well-known methods, such as the Seldinger technique. More particularly, the anchoring catheter preferably tracks over a pre-installed guide wire (not shown) that has been inserted into the subclavian vein and steered through the vasculature until it resides at the apex of the right ventricle. The physician advances the anchoring catheter along the guide wire until its distal tip is touching or adjacent to the apex of the right ventricle RV (the location of the device anchor 24 in FIG. 1).

After installing the device anchor 24 at or near the apex of the right ventricle RV, the surgeon retracts the anchoring catheter and removes it completely from the patient's body in favor of the delivery catheter 32, described below. The exemplary device anchor 24 includes a plurality of circumferentially distributed and distally-directed sharp tines or barbs that pierce the tissue of the ventricular apex. Although the particular device anchor 24 shown in FIG. 1 is considered highly effective, other anchors are contemplated, and the application should not be considered limited to one type or another. More details of the device anchor 24 and alternatives, and of the regurgitation reduction system 20 in general, are provided in U.S. Patent Publication No. 2013/0338763, the entire contents of which are expressly incorporated herein.

To facilitate central positioning of the anchor rail 26 during deployment the device is implanted with the assistance of a visualizing device, for example, a fluoroscope and/or an ultrasound imager. In a preferred embodiment, the anchor 24 is preferably located in the base of the ventricle between the septum (or inner) wall SW and the free (or outer) wall. Aligning the anchor rail 26 in this manner helps center the eventual positioning of a coapting element 34 of the system within the tricuspid leaflets. An entire coapting element 34 offset to the anterior or posterior side may get stuck in the tricuspid valve commissures, resulting in leakage at the center of the valve. An alternative method is to place a device such as a Swan-Ganz catheter through the right ventricle and into the pulmonary artery to verify that the viewing plane is parallel to the anterior/posterior viewing plane. Addition of a septal/lateral view on the fluoroscope may be helpful in centering the anchor in patients that have a dilated annulus and right ventricle.

The surgeon then advances the delivery catheter 32 advanced along or over the anchor rail 26 to position the coaptation element 34 within the tricuspid valve TV. Ultimately, the coaptation element 34 resides within the tricuspid valve TV, the leaflets of which are shown closed in systole and in contact with the coaptation element. The delivery catheter 32 remains in the body as seen, and the prefix "delivery" should not be considered to limit its function.

The physician ensures or confirms proper positioning of the coaptation element 34 within the tricuspid valve TV, then locks the delivery catheter 32 with respect to the anchor rail 26 by actuating the locking collet 40, and then severs that portion of the delivery catheter 32 that extends proximally from the locking collet. The collet 40 and/or coiled portion of the delivery catheter 32 may be sutured or otherwise anchored in place to subcutaneous tissues outside the subclavian vein SV. The subcutaneous positioning of the collet 40 permits future adjustment of the coaptation element to improve or correct any residual or later developing regurgitation. Notably, because the delivery catheter 32 slides with respect to the anchor rail 26, it may be completely removed to withdraw the coaptation element 34 and abort the procedure, either during or after implantation. The implant configuration is similar to that practiced when securing a pacemaker with an electrode in the right atrium muscle tissue and the leads extending to the associated pulse generator placed outside the subclavian vein. Indeed, the procedure may be performed in conjunction with the implant of a pacing lead. For example, in some embodiments, a pacing lead is placed contemporaneously with but independently of the anchor rail. In other embodiments, a pacing lead is placed first and used as a rail or guidewire for an anchor rail that advances over the pacing lead. In another embodiment, a pacing lead serves as the anchor rail. In other embodiments, the anchor rail is modified to include the features of a pacing lead.

Other embodiments include one or more locking mechanisms either together with or instead of the locking collet 40 for locking the position of the coaptation element 34 within the tricuspid valve TV and relative to the fixed anchor rail 26, and the application should not be considered limited to the illustrated embodiment. For instance, rather than a locking collet 40, a crimpable section or portion made from a biocompatible material, such as a stainless steel tube, may be included on the delivery catheter 32 at a location near the skin entry point and spaced apart from the location of the coaptation element 34. The physician need only position the coaptation element 34 within the leaflets, crimp the crimpable section of the catheter 32 onto the anchor rail 26, and then sever both the catheter and rail above the crimp point.

Given the close proximity of a preferred anchoring site to the septal wall SW, the flexible rail 26 and coaptation element 34 typically exhibit a strong septal bias. Significant impact between the coaptation element 34 and the septal wall SW has been observed on ultrasound echo imaging in animal testing, leading to possible malformation of the coaptation element 34 as will be described.

Several coaptating elements are described herein, each of which is an embodiment of the coaptation element 34 shown in FIG. 1.

FIGS. 2 and 2A-2B shows an axi-symmetric coaptating element 50 with an outer generally cylindrical cover 52 having closed ends surrounding an elongated tubular compressible member 54. The compressible member 54, in turn, mounts around an inner catheter 56 that has perforations 58 for adding and removing air or other fluid from the compressible member, as indicated by FIGS. 3A and 3B in systole and diastole, respectively. At least a portion of the compressible member 54 may be an open cell foam. In this way, the coaptation element 50 may be compressed to reduce its size for delivery, and then increased after implant. In one embodiment, the coaptation element 50 has a diameter in its uncompressed state of about 10 mm. For example, in some embodiments, air in the open cell foam of the coaptation element is replaced with a physiologically compatible fluid, for example saline, in a process comprising fluidly connecting the coaptation element with a vacuum source to remove air from the open cell foam thereof, then contacting the coaptation element with the physiologically compatible fluid with the air and saline flowing out of and into the open cell foam through the perforations. The coaptating element is then compressed or collapsed to a delivery diameter. After deployment in a patient's tricuspid valve, the coaptation element reexpands, refilling the open cell foam with fluid, for example, blood, through the perforations.

The inner catheter 56 has an inner lumen sized to slide over the flexible rail 26, and corresponds to the delivery catheter 32 described above. The cover 52 functions something like a balloon, and is desirably formed of a thermoplastic polyurethane such as CARBOTHANE® polycarbonate-based thermoplastic polyurethane (TPU) (Lubrizol Corp., Wickliffe, Ohio). The catheter 56 is also preferably made from a material that is bondable to the cover 52, for example, the same material (e.g., CARBOTHANE® TPU) so that the distal and proximal necks of the cover 52 can easily be heat bonded thereto for a good seal, and is desirably reinforced with braiding to provide good inner support for the pressures generated within the cover 52.

The coaptating element 50 is axi-symmetric, with the throughbore in the tubular compressible member 54 centered so that the inner catheter 56 is also centered. Multiple chronic animal implants of the coaptation element 50 reveals foam compression and subsequent wrinkling of the polymer balloon, analogous to cover 52, most likely from impact between the coaptation element 50 and the septal wall SW, especially during diastole. While the coaptation element 50 in this state potentially retains at least some functionality, the wrinkles on the balloon could eventually lead to one or both of the following complications: (1) native tricuspid leaflet damage due to higher localized impact forces against a stiffer and rougher surface, and (2) peri-device leak (TR) due to blood leakage through small channels formed between folds of the wrinkles. While manipulating or adjusting the amount of slack in the railing system 26 can help position the coaptation element 50 at most points along the anterior-posterior axis, limited positional control in the septal-lateral axis is available (mostly due to the angle of the superior vena cava SVC in relation to the valve plane). Increasing foam stiffness is one possible solution to resist compression and wrinkles; however, stiffer foams limit deliverability through small introducer sheaths.

Another embodiment includes an "offset" foam-filled balloon design, and an associated method of in-vivo positioning for reducing or mitigating foam compression and/or balloon wrinkling in the coaptation element 34 from interaction with the septal wall SW. The design relies on an offset balloon shape, in which the delivery catheter is not coaxial with the balloon body, but rather offset radially, almost completely to one side in some embodiments. This results in a circumferentially asymmetrical design with "spine" and "belly" regions, where nearly the entire foam cylinder sits on the "belly" side of the coaptation shaft (which serves as the "spine"). Once delivered down to the tricuspid valve plane over the railing shaft, the offset coaptation element can be rotated freely until the "spine" aligns towards the septal wall (using, for example, fluoroscopic guidance). The axial, lateral, and rotational position of the device is then locked via a collet clamping mechanism, for example, any of the mechanisms described above. In the desired orientation, if the device impacts the septal wall, nearly all the impact force is absorbed by the relatively stiff reinforced coaptation shaft and railing shaft rather than the relatively soft and compressible foam. Therefore, embodiments of this design resist damage from impact with the septal wall SW, thereby reducing or minimizing the risk of foam compression and subsequent balloon wrinkling.

FIGS. 4 and 4A-4B shows an embodiment of an offset coapting element 70 with an outer, generally cylindrical cover 72 having closed ends surrounding an elongated compressible member 74. The compressible member 74, in turn, mounts around or against an inner catheter 76 that has perforations 78 for adding and removing air or fluid from the compressible member, such as indicated by the earlier FIGS. 3A and 3B in systole and diastole, respectively. As discussed above, all or a portion of the compressible member 74 may be an open cell foam, and the size of the coaptation element 70 may be thus reduced for delivery and increased after implant.

The inner catheter 76 has an inner lumen sized to slide over the flexible rail 26, and corresponds to the delivery catheter 32 described above. The cover 72 and catheter 76 are also desirably formed of a thermoplastic polyurethane such as CARBOTHANE® TPU. The catheter 76 may be reinforced with braiding to provide good inner support for the pressures generated within the cover 72.

Rather than a symmetric configuration, the compressible member 74 has a generally outwardly cylindrical shape but an inner lumen 80 that is offset from its central axis, and preferably is located adjacent to or immediately against an outer wall 82 thereof. In this way, the compressible member 74 is offset with respect to the central axis of the inner catheter 76 positioned within the inner lumen 80, as best seen in FIGS. 4A and 4B. Stated another way, the coaptation member 70 has a generally cylindrical shape and the compressible inner filler member 74 is mounted on the delivery catheter 76 so that a majority of the filler member is axially offset from the central axis of the delivery catheter. This results in a circumferentially asymmetrical design with a "spine" region on one diametric side of the inner catheter 76 (the catheter being the spine), and a "belly" region opposite thereto comprising nearly the entire foam cylinder. The spine side on which the inner catheter 76 is located is then oriented toward the septal wall SW to provide stiffness and resistance to deformation from repeated contact therewith.

In one configuration, the coaptation element 70 has a diameter in its uncompressed state of about 10 mm, while the inner catheter 76 has an outer diameter of 2-3 mm. Therefore, the catheter 76 does not lie on the central axis of the compressible member 74.

While echocardiography could potentially aid rotational orientation of the offset coaptation element 70, in the illustrated embodiment, a fluoroscopic method is preferred due to superior resolution and less interference from surrounding structures. In a preferred embodiment, fluorescent or radiopaque markers are included on the coaptation element 70 to indicate the rotational orientation thereof.

FIGS. 5-8 illustrate a series of fluoroscopic images of the coaptation element 70 in four different rotational orientations, as viewed from the typical right lateral fluoroscopic projection. In the first image, FIG. 5A, the coaptation element 70 is oriented with the spine or inner catheter 76 to the back side and against the septal wall SW, as seen in the sectional view of FIG. 5B. The septal wall SW is in the plane of the page, the free wall is parallel to the septal wall SW in front of the page, anterior to the right, and posterior to the left.

As shown in FIGS. 9A-9D, a set of C-shaped radiopaque marker bands 90, 92 are mounted, printed, or otherwise disposed on the inner catheter 76 in order to aid rotational positioning of the offset coaptation element 70. In the preferred orientation as seen in FIGS. 5A and 5B, an upper marker band 90 shows up on the fluoroscope on the left side of the catheter 76, while a lower marker band 92 shows up on the right side. The size of the two marker bands 90, 92 in this orientation is such that they appear to be approximately the same size and extending from the midpoint of the catheter 76 in opposite directions. A direct view of the coaptation element 70 in this orientation is seen in FIG. 9A. If the coaptation element 70 rotates from this preferred orientation, the appearance of the marker bands 90, 92 changes, as described below.

In particular, FIG. 6A is a fluoroscopic image of the coaptation element 70 rotated approximately 30° in a clockwise direction, as seen from above, which is depicted in section in FIG. 6B. The marker bands 90, 92 look somewhat different, with the lower band 92 having rotated more into the field of view and thus being wider and occluding the image of the catheter 76 at that location. Again, a direct view of the coaptation element 70 this orientation is seen in FIG. 9B. The inner catheter 76 has rotated away from the septal wall SW, thus exposing a softer portion of the coaptation element 70 to possible deformation.

Next, FIG. 7A shows the coaptation element 70 rotated approximately 90° from the preferred orientation of FIG. 5A in a clockwise direction as seen from above, which is depicted in section in FIG. 7B. The inner catheter 76 has rotated farther away from the septal wall SW, exposing more of the compressible portion of the coaptation element 70 to possible deformation. The marker bands 90, 92 look somewhat different, with the upper and lower bands 90, 92 having rotated further and appear their widest, totally across the catheter 76. Again, a direct view of the coaptation element 70 this orientation is seen in FIG. 9C.

And finally, in FIG. 8A the coaptation element 70 is rotated completely 180° from the preferred orientation of FIG. 5A, as depicted in section in FIG. 7B, and the marker bands 90, 92 are essentially opposite from the view of FIG. 5A. That is, the upper marker band 90 shows up on the fluoroscope on the right side of the catheter 76, while the lower marker band 92 shows up on the left side. This orientation is seen from above in FIG. 9D. The spine of the coaptation element 70 is oriented away from the septal wall SW, which means the belly or soft portion of the device is subject to contact with the septal wall SW, and may be subject to wrinkling.

The C-shaped marker bands 90, 92 placed in this manner allow a physician to distinguish between the various angular orientations. The marker bands 90, 92 assume a unique relative position when the coaptation element 70 is in the proper orientation with the "spine" toward the septal wall SW. The semi-tubular shape and axial spacing of the marker bands 90, 92 are able to distinguish between the positions 180° apart. Of course, other arrangements of markers are possible, the C-shaped marker bands 90, 92 being exemplary only. For example, some embodiments include rotational orientation markers on the balloon and/or a balloon that is shaped to show the rotational orientation thereof.

In validity studies on animals, the ability to use fluoroscopic guidance to achieve correct rotational position of the offset coaptation element 70, and to assess the rotational stability of the offset coaptation element 70 after locking the proximal collet was confirmed. Further, the studies determined that the coaptation element 70 resisted any rotational shifts due to impact with native leaflets and/or the septal wall. In the studies, the device was delivered, and the radiopaque C-markers enabled the desired rotational positioning (confirmed by echocardiography and fluoroscopy). The proximal collet was locked and the shafts were coiled and tucked into a subcutaneous pocket per protocol. The device was deployed in the animal for a total of at least three hours. After this waiting period, echocardiographic and fluoroscopic examinations were repeated, and all images indicated that the rotational position of the offset coaptation element 70 had not shifted. Upon examination of the device at explant, the "spine" of the offset coaptation element 70 appeared to be correctly positioned towards the septal wall, and no foam compression or balloon wrinkling was observed.

Some embodiments include a softer foam on the offset coaptation element 70 that permits delivery through a significantly smaller sheath, even without additional components (e.g., a delivery system). Stiffer foams are inherently denser, and in some instances, cause shadowing of surrounding structures on echocardiography. Some embodiments including softer foam on the offset coaptation element 70 improve or maximize the visibility of surrounding structures (e.g., native leaflets), the imaging of which facilitate the correct longitudinal positioning of the device.

Alternatively, the "spine" formed by the catheter 76 could be offset to any degree between the center axis of the balloon body and the outer circumference of the balloon. Also, the foam filling need not be homogenous or entirely made from a single material. For example, some embodiments include a small section or portion of a significantly stiffer foam selectively placed or positioned in the thin slice or region between the spine and septal surface of the balloon. Further, the coaptation element 70 could have any suitable non-circular shape (e.g., oval, ellipse, triangle) in order to better fit the annulus/regurgitant orifice.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A heart valve coaptation system for reducing regurgitation through the valve, comprising:
    a flexible rail having a ventricular anchor on a distal end thereof adapted to anchor into tissue within a ventricle;
    a delivery catheter having a lumen defining a central axis through which the flexible rail passes and including a locking mechanism for fixing relative axial positions of the delivery catheter and flexible rail; and
    a coaptation member fixed on a distal end of the delivery catheter having an outer cover surrounding a compressible inner filler member and a generally cylindrical shape, the compressible inner filler member being mounted on the delivery catheter so that a majority of the filler member is radially offset from the central axis of the delivery catheter and the delivery catheter lies along one radial side thereof to form an offset spine of the coaptation member, wherein
    the compressible inner filler member is an open cell foam that fills the space between the delivery catheter and the outer cover, and wherein
    there are two types of open cell foam, with a majority being a first foam and a significantly stiffer second foam positioned in a thin region along the one radial side between the delivery catheter and outer cover.

2. The system of claim 1, wherein the delivery catheter includes a series of perforations along a length that is located within the coaptation member to permit gas or fluid flow between pores in the filler member and an inner lumen of the catheter.

3. The system of claim 1, wherein the ventricular anchor includes a plurality of circumferentially distributed and distally-directed sharp tines or barbs that pierce the tissue within a ventricle.

4. The system of claim 1, wherein the coaptation member has a diameter in its uncompressed state of about 10 mm, while the delivery catheter has an outer diameter of 2-3 mm.

5. The system of claim 1, wherein the outer cover of the coaptation member is adhered around the delivery catheter so as to be closed on both ends and form a chamber outside of the delivery catheter.

6. The system of claim 5, wherein both the outer cover and the delivery catheter are made of the same material.

7. The system of claim 6, wherein both the outer cover and the delivery catheter are made of a polycarbonate-based thermoplastic polyurethane.

8. The system of claim 1, further including at least one radiopaque marker on the delivery catheter or coaptation member that shows up as different shapes for different rotational orientations when viewed with a fluoroscope.

9. The system of claim 8, wherein the at least one radiopaque marker comprises a pair of C-shaped radiopaque markers bonded to the delivery catheter at different locations.

10. A heart valve coaptation system for reducing regurgitation through the valve, comprising:
    a flexible rail having a ventricular anchor on a distal end thereof adapted to anchor into tissue within a ventricle;
    a delivery catheter having a lumen defining a central axis through which the flexible rail passes and including a locking mechanism for fixing relative axial positions of the delivery catheter and flexible rail; and
    a coaptation member fixed on a distal end of the delivery catheter comprising a compressible member having a radial cross-sectional shape larger than a cross-section of the delivery catheter, the compressible member extending across a radial cross-section of the coaptation member and being configured to enable passive expansion of the coaptation member from a compressed state, the delivery catheter being mounted within the cross-sectional shape so as to lie along one diametric side thereof so that a majority of the compressible member is axially offset from a central axis of the delivery catheter, the delivery catheter being formed of a material that is relatively stiffer than the compressible member to form a spine while the compressible member forms a belly, wherein the coaptation member has an outer cover surrounding a compressible inner filler member, wherein the compressible inner filler member is an open cell foam that fills the space between the delivery catheter and the outer cover, and wherein there are two types of open cell foam, with a majority being a first foam and a significantly stiffer second foam positioned in a thin region along the one diametric side between the delivery catheter and outer cover.

11. The system of claim 10, wherein the coaptation member has a generally cylindrical shape.

12. The system of claim 10, wherein the delivery catheter includes a series of perforations along a length that is located within the coaptation member to permit gas or fluid flow between pores in the filler member and an inner lumen of the catheter.

13. The system of claim 10, wherein the outer cover of the coaptation member is adhered around the delivery catheter so as to be closed on both ends and form a chamber only open to the perforations.

14. The system of claim 13, wherein both the outer cover and the delivery catheter are made of the same material.

15. The system of claim 10, wherein the ventricular anchor includes a plurality of circumferentially distributed and distally-directed sharp tines or barbs that pierce the tissue within a ventricle.

16. The system of claim 10, wherein the coaptation member has a diameter in its uncompressed state of about 10 mm, while the delivery catheter has an outer diameter of 2-3 mm.

17. The system of claim 10, further including at least one radiopaque marker on the delivery catheter or coaptation member that shows up as different shapes for different rotational orientations when viewed with a fluoroscope.

18. The system of claim 17, wherein the at least one radiopaque marker comprises a pair of C-shaped radiopaque markers bonded to the delivery catheter at different locations.

* * * * *